United States Patent [19]

Ratigan

[11] 4,444,058

[45] Apr. 24, 1984

[54] METHOD AND APPARATUS FOR DETERMINING TENSILE STRENGTH

[75] Inventor: Joe L. Ratigan, Rapid City, S. Dak.

[73] Assignee: The United States of America as represented by the United States Department of Energy, Washington, D.C.

[21] Appl. No.: 382,997

[22] Filed: May 28, 1982

[51] Int. Cl.³ .............................................. G01N 3/08
[52] U.S. Cl. .................................................. 73/834
[58] Field of Search .................. 73/834, 803, 821, 832

[56] References Cited

U.S. PATENT DOCUMENTS

| 756,644 | 4/1904 | Johnson | 73/803 |
|---|---|---|---|
| 3,111,840 | 11/1963 | Barnet et al. | 73/837 |
| 3,122,916 | 3/1964 | Sedlacek | 73/837 |
| 3,792,608 | 2/1974 | Holm et al. | 73/803 |
| 3,934,464 | 1/1976 | McCauley | 73/837 |

FOREIGN PATENT DOCUMENTS 1605003 10/1972 France ................................. 73/803
1312764 4/1973 United Kingdom ................. 73/803

OTHER PUBLICATIONS

Report LBL-13286 "A Statistical Fracture Mechanics Approach to the Strength of Brittle Rock," J. L. Ratigan, Ph.D. Thesis, University of California, Berkeley, Calif., Jun. 1981.

Primary Examiner—Anthony V. Ciarlante
Attorney, Agent, or Firm—L. E. Carnahan; Roger S. Gaither; Michael F. Esposito

[57] ABSTRACT

A method and apparatus for determining the statistical distribution of apparent tensile strength of rock, the size effect with respect to tensile strength, as well as apparent deformation modulus of both intact and fractured or jointed rock. The method is carried out by inserting a plug of deformable material, such as rubber, in an opening of a specimen to be tested. The deformable material is loaded by an upper and lower platen until the specimen ruptures, whereafter the tensile strength is calculated based on the parameters of the test specimen and apparatus.

10 Claims, 1 Drawing Figure

METHOD AND APPARATUS FOR DETERMINING TENSILE STRENGTH

BACKGROUND OF THE INVENTION

The invention described herein arose at the Lawrence Berkeley Laboratory in the course of, or under, Contract No. W-7405-ENG-48 between the U.S. Department of Energy and the University of California.

The invention relates to determining apparent tensile strength of a material, particularly to determining the tensile strength of rock, and more particularly to method and apparatus for determining the tensile strength and/or the deformation modulus of rock by rubber fracturing.

In a majority of rock mechanics problems, the engineer is seldom concerned with the tensile strength of intact rock, for the inherent discontinuities are the predominant structural component that usually determines the strength of the rock mass. However, there are a limited number of important situations wherein the knowledge of the apparent tensile strength of intact rock is of fundamental importance. For example, a knowledge of the apparent tensile strength in a hydraulic fracture experiment for the determination of in situ stress is fundamentally necessary if the state of stress is to be determined from the initiation of the hydraulically induced fracture.

In certain underground situations, such as the apparent tensile strength of intact rock beams defined by jointing or bedding planes is important in determining required rock bolting. Proposed high technology uses of underground cavities such as for liquid petroleum gas (LPG) storage require a knowledge of apparent tensile strength of the material of the surrounding walls, particularly as it relates to cyclic loading and potential fatigue failure. Also the apparent tensile strength and or deformation modulus of rock is of use to those involved in the application of hydraulic fracturing for the determination of in situ stress or for recovery of natural gas or other hydro-carbon deposits in relatively impermeable formations.

When intact rock samples are taken into the laboratory and tested to determine tensile strength, three observations should be made:

(1) The apparent tensile strength depends upon the sample size (the larger the specimen, the smaller the strength).

(2) The apparent tensile strength depends upon the type of test being performed.

(3) With any given test and specimen size, a scatter (usually skewed) about the mean is obtained.

The first of the above-listed three observations (commonly referred to as the size effect) is also observed with respect to compressive strength and an apparent Young's Modulus, although to a lesser extent than with tensile strength. However, this first observation has prompted many investigators to recognize that the tensile strength of brittle rock measured at the usual laboratory scale is not a material property.

The second of the above-listed observations has been brushed aside by using different names to refer to the strength observed in different tests. For example, the apparent tensile strength in bending is referred to as the Modulus of Rupture. The tensile strength determined by indirect tension tests is often referred to with an adjective taken from the test; for example, the Brazilian tensile strength or the split cylinder tensile strength.

The third above-listed observation is often totally neglected in the reporting of test results. Scatter about the mean is often attributed to testing methodology and/or sample-to-sample inhomogenity. Thus, more often than not, the only result of the tensile testing may be the mean without the standard deviation or any of the other statistical moments.

The "direct" tensile strength test is effected by loading a cylindrical or prismatic specimen in tension to failure. The specimen should fall in plane tensile stress and, for homogeneous isotropic material, the plane of failure should be normal to the axis of the specimen. The precautions are twofold: first, the applied tensile load must be uniformly distributed over the end of the specimen and parallel to its axis; second, the method of holding the specimen must not produce significant lateral stress in the specimen. To minimize the effects of this, the central section of metal tensile strength specimens is usually machined to a smaller diameter. With rock, this is a difficult operation.

It is known that even small scratches on the surface of metal specimens will reduce the tensile strength appreciably and some investigators fine-grind or polish the cylindrical surface of rock specimens to minimize this effect. However, most rock contains planes of weakness, incipient cracks, or other mechanical defects, and failure usually occurs at the point of these defects, a factor that causes a comparatively large deviation in the tensile strength measurements from a group of specimens. Also, as the length of tensile strength specimens is increased, the probability of including a weaker defect is increased and, hence, the average tensile strength decreases with the size of test specimens.

As pointed out above, two most commonly used testing methods are: The Brazilian Test; and the Modulus of Rupture Test. In the Brazilian Test, a cylindrical test specimen is placed horizontally between the bearing plate of a testing machine and loaded to failure in compression. If a line load is applied in a plane passing through the diameter of the cylindrical specimen from both directions, a uniform tensile stress should develop across the plane. However, in addition to the tensile strength that develops across the diametrical plane, a vertical compressive stress occurs in the plane. This compressive stress causes high shear stresses and local crushing along the loading line. This failure has been solved by applying the load to a strip of desired width.

The Modulus of Rupture Test is a measure of the outer fiber tensile strength of a material. This property is determined by loading either cylindrical or prismatic specimens in a three-point loading device to failure. In the loading device used for testing prismatic specimens, two of the bearing edges must be self-aligning (pivoted) to permit uniform loading of the specimen surfaces when such are not exactly parallel. Self-aligning bearing edges are not required for testing cylindrical specimens. The ends of the specimens do not need to be surfaced. The specimen should be loaded to failure at a uniform rate of 500 psi/min.

Although the Modulus of Rupture Test is a measure of the outer-fiber tensile strength of a material, the value obtained by this procedure is higher than determined in the "direct" Test. This higher value is presumed to result from the fact that only a small area (or point) on the opposite side of the specimen directly under the point is subject to the maximum tensile strain. Hence, the probability of a defect occurring at or near this point is less than that for an equivalent defect occurring in the length of a tensile specimen.

Various types of apparatus have been developed for testing samples or specimens of different types of material. For example, U.S. Pat. No. 756,644 issued Apr. 5, 1904 to A. N. Johnson and U.S. Pat. No. 3,122,916 issued Mar. 3, 1964 to R. Sedlacek relate to insertion of a rubber member into a borehole of a specimen to be tested and inflating the rubber member causing fracturing of the specimen. Further, U.S. Pat. No. 3,111,840 issued Nov. 26, 1963 to F. R. Barnet et al, U.S. Pat. No. 3,792,608 issued Feb. 19, 1974 to T. A. Holm et al, and U.S. Pat. No. 3,934,464 issued Jan. 27, 1976 to C. R. McCauley teach testing of a specimen of material by applying pressure of various types to the specimen causing fracturing thereof.

While the prior known methods and apparatus for carrying out the prior methods have been effective, at least to a certain extent, to provide the tensile strength of various materials, such have not been effective in determining the apparent tensile strength of rock and/or the apparent deformation modulus of rock. Thus, a need has existed for a more effective method of providing desired information relative to rock formations.

Therefore, it is an object of this invention to provide a method and apparatus for effectively determining the tensile strength and/or deformation modulus of rock.

A further object of the invention is to provide a rubber fracturing method and apparatus for determining the apparent tensile strength and/or deformation modulus of rock.

Another object of the invention is to provide a method of testing the tensile strength of a rock specimen by inserting a non-inflatable, deformable member in a borehole in the specimen and applying pressure to the deformable member causing rupturing of the specimen.

SUMMARY OF THE INVENTION

The present invention fills the above-referenced need in the art by providing a simple but effective method and apparatus for determining the tensile strength and/or deformation modulus of rock. The method and apparatus of this invention is accomplished through rubber fracturing of disks of rock. A circular rock disk with a concentric inner borehole is loaded by insertion of a short piece of deformable material, such as synthetic rubber. The rock disk is then placed between an upper platen and a lower platen. As the upper platen is loaded by the application of force perpendicularly thereto, the rubber insert is compressed longitudinally and expanded radially, which causes the rock disk to fracture. The apparent tensile strength or deformation modulus of the rock can then be calculated.

BRIEF DESCRIPTION OF THE DRAWING

The single FIGURE is an exploded view of an embodiment of the apparatus made in accordance with the invention.

DETAILED DESCRIPTION OF THE INVENTION

Figure 1:
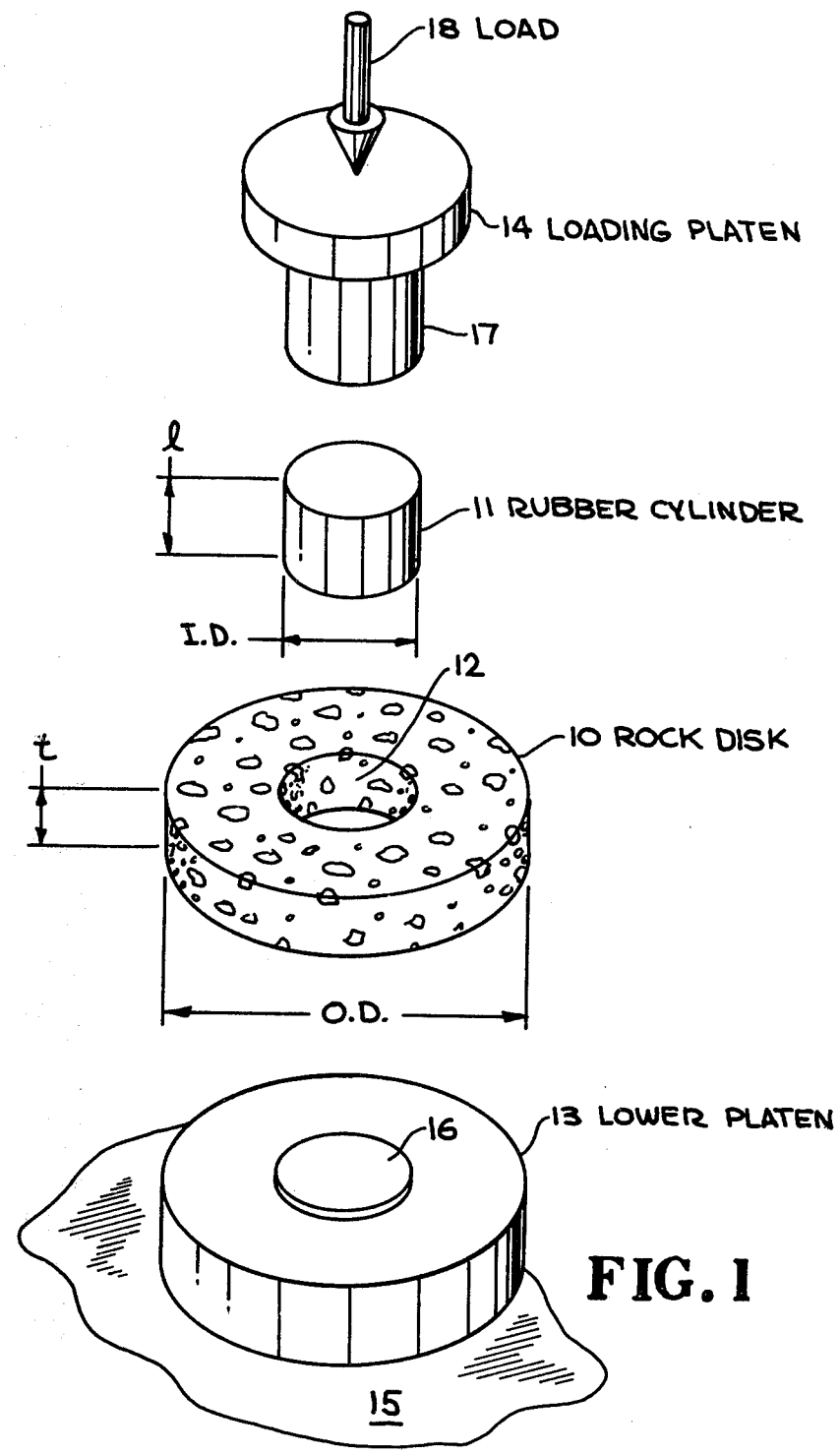

The present invention involves a method and apparatus for the determination of apparent tensile strength through rubber fracturing of disks of rock. Basically, a circular rock disk with a concentric inner borehole is loaded on the internal surface until rupture occurs at the apparent tensile strength. The loading of the internal borehole is accomplished with two loading platens and a cylinder of non-inflatable deformbable material, such as rubber. As one of the platens is loaded by the application of force perpendicularly thereto, the rubber cylinder is compressed longitudinally and expanded radially, which causes the rock disk to fracture.

The method of this invention, referred to herein as rubber fracturing, is a simple method of determining the statistical distribution of apparent tensile strength of rock, the size effect with respect to tensile strength, as well as apparent deformation modulus of both intact and fractured or jointed rock. The rubber fracturing method of this invention is generally similar to the conventional hydraulic fracturing method. However, in the rubber fracturing method the rock specimen is significantly smaller in the axial dimension and the loading is provided by rubber rather than fluid.

The invention has been utilized in tests performed on Stripa granite.

The tests conducted in verifying the invention as well as information relative to statistical fracture mechanics, fracture mechanics models, etc., are set forth in a Ph.D. Thesis, "A Statistical Fracture Mechanics Approach to the Strength of Brittle Rock," J. L. Ratigan, dated June 1981, University of California, Berkeley, CA.

The virtues of the rubber fracturing method of this invention are that it is easily performed, requires a minimum amount of equipment, and allows a rapid determination of the empirical tensile strength size effect.

The rock specimens for the rubber fracturing method are fabricated from conventionally obtained rock cores. The core is "sliced" into thin disks with a diamond saw. The diamond sawed surfaces need not be milled or treated in any other manner since they are not loading surfaces. A concentric hole is diamond drilled through the rock disk. For example, in tensile strength tests conducted utilizing the invention, the rock disk specimens had an outside diameter (O.D.) of 62 mm, a thickness (t) of 12.7–25.7 mm, and a concentric hole or inside diameter (I.D.) of 6.4–12.7 mm.

Referring now to the drawing, a rock disk 10 configured as described above, is fitted with a short plug or cylinder 11 of deformable material, such as synthetic rubber (Buta-N) cording stock, in a central borehole 12 of disk 10 such that a distance of 1 mm (axial length), for example, exists on both the upper and lower portions of the central borehole 12. The deformable material cylinder 11 thus has a length (l) of t-2 mm, with t being the thickness of disk 10, and an outer diameter of slightly less than the central borehole (I.D.) 12 of disk 10.

The loading apparatus consists of a lower platen 13 and an upper platen (loading platen) 14, platen 13 being positioned on a support member indicated at 15. Lower platen 13 is provided with a protruding central section or lip 16, while upper platen 14 is provided with a similar, but longer protruding section 17. The length of protruding section 16 is, for example, 1 mm such that when disk 10 is positioned on platen 13 the upper end of section is in abutting relation with cylinder 11. The outer diameter of platen sections 16, 17 is substantially the same as the outer diameter of cylinder 11, and thus just slightly less than the diameter of central borehole 21 of disk 10.

The loading apparatus also includes a loading frame, not shown, similar to that used in most testing laboratories, for support of the platens and applying a downward loading force to the upper platen.

The upper platen 14 is loaded steadily at a relatively low rate, as indicated by the load arrow 18, until the rock disk or specimen 10 ruptures. As the platen is loaded, the rubber cylinder 11 is compressed longitudinally and expanded radially. This places the disk 10 under tension. The apparent tensile strength is then calculated by the formula:

$$T_A = (P/A)\alpha$$

Where:
$T_A$ = apparent tensile strength
P = load at rupture
A = cross-sectional area of the rubber cylinder
$\alpha = [(b/a)^2 + 1]/[(b/a)^2 - 1]$
b = radius of core disk
a = radius of internal borehole By way of example, with a disk of Stripa granite having an outside diameter (O.D.) of 62 mm, a central borehole (inside diameter) of 6.4 mm, and a thickness (t) of 12.7, the rate at which the upper platen is loaded is 600 psi/min.

If the associated load/deformation is recorded, the apparent deformation modulus can also be calculated once the properties of the rubber cylinder have been determined independently.

It has thus been shown that the rubber fracturing method of determining apparent tensile strength provided by this invention provides a unique method of testing in that is is a simple and inexpensive method of determining empirical size effect. The method of this invention is particularly of use for those involved in the application of hydraulic fracturing for determination of in situ stress, for recovery of natural gas or other hydrocarbon deposits in relatively impermeable formations, or for determining the tensile strength of the wall of underground cavities.

While the above-described method has particular application in the determination of the apparent tensile strength of rock, it may be used, as pointed out above, to determine the apparent deformation modulus of rock, not only for intact rock, but also for fractured or jointed rock.

Although the invention has been described as utilizing certain parameters, materials, and apparatus, it is not intended to limit the invention to the specifies thus described, and it is intended to cover in the appended claims all that comes within the scope of this invention.

What I claim is:

1. In a method for the determination of apparent tensile strength of rock, the improvement including the steps of:
    forming a non-inflatable, substantially solid, cylindrically shaped deformable member so as to have a length less than a length of an opening extending through a rock specimen to be tested,
    inserting the deformable member into the opening extending through the specimen to be tested,
    providing load applying means configured to have protruding portions thereon for extending into the opening of the rock specimen,
    positioning the load applying means on opposite sides of the deformable member such that the protruding portions of the load applying means abuts opposite ends of the deformable member, and
    applying a force to the load applying means causing longitudinal compression and radial expansion of the deformable member which causes fracturing of the rock specimen.

2. The improvement of claim 1, additionally including the step of forming the deformable member as a rubber cylinder.

3. The improvement of claim 1, additionally including the step of forming the rock specimen so as to have a disk configuration with the opening therethrough being located substantially centrally therein.

4. A rubber fracturing method for determining the tensile strength of rock including the steps of:
    inserting a substantially solid rubber member in an aperture in a rock disk specimen to be tested such that the rubber member length is less than the length of the aperture in the rock disk,
    positioning the rock disk specimen between a pair of platens having protruding sections thereof such that the protruding sections of the platens extend into the aperture in the rock disk and are in abutment with opposite ends of the rubber member, and
    applying force to the rubber member through at least one of the pair of platens causing at least radial expansion of the rubber member resulting in fracturing of the rock disk specimen.

5. The method of claim 4, additionally including the step of calculating the apparent tensile strength of the rock disk specimen by the formula:

$$T_A = (P/A)\alpha$$

Where:
$T_A$ = apparent tensile strength
P = load at rupture
A = cross-sectional area of the rubber member
$\alpha = [(b/a)^2 + 1]/[(b/a)^2 - 1]$
b = radius of the rock disk
a = radius of the rock disk aperture.

6. The method of claim 4, additionally including the step of forming the rock disk specimen by:
    slicing a rock core to form the disk, and
    forming the aperture in the rock disk by drilling a concentric hole through disk.

7. The method of claim 4, additionally including the step of forming the protruding sections of the pair of platens so as to have an outer diameter of approximately the same as an outer diameter of the rubber member.

8. The method of claim 4, additionally including the step of forming the rubber member so as to have a cylindrical configuration, an outer diameter slightly less than a diameter of the aperture in the rock disk into which the rubber member is to be inserted, and a length less than a length of a rock disk aperture into which the rubber member is to be inserted.

9. An apparatus for rubber fracturing rock disks to determine the apparatus tensile strength of the rock comprising:
    a substantially solid cylindrically shaped deformable rubber member having opposite end surfaces and adapted to be inserted into a central borehole of a rock disk to be tested,
    a first platen having a protruding section adapted to be inserted into the central borehole of a rock disk to be tested and in abutment with one of said end surfaces of said deformable member,
    a second platen having a protruding section adapted to be inserted into the central borehole of a rock disk to be tested and in abutment with an opposite one of said end surfaces of said deformable member, and means for applying a load to said deformable member through at least one of said end surfaces by at least one of said platens causing said deformable member to be compressed longitudinally and expanded radially, thereby placing the rock disk to be tested under tension and resulting in fracturing of the rock disk.

10. The apparatus of claim 9, wherein said deformable member is constructed so as to have an outer diameter slightly less than a diameter of a central borehole of a rock disk to be tested into which the deformable member is to be inserted, and is constructed so as to have a length less than a length of a central borehole of a rock disk to be tested into which the deformable member is to be inserted.

* * * * *